US008785193B2

(12) United States Patent
Shin

(10) Patent No.: US 8,785,193 B2
(45) Date of Patent: Jul. 22, 2014

(54) DISSECTION TOOL AND METHODS OF USE

(75) Inventor: Soojung Shin, Carlsbad, CA (US)

(73) Assignee: The United States of America, as represented by the Secretary of the Department of Health and Human Services, Washington, DC (US)

(*) Notice: Subject to any disclaimer, the term of this patent is extended or adjusted under 35 U.S.C. 154(b) by 2191 days.

(21) Appl. No.: 11/531,972

(22) Filed: Sep. 14, 2006

(65) Prior Publication Data

US 2008/0066322 A1    Mar. 20, 2008

(51) Int. Cl.
*C12N 5/00*    (2006.01)
(52) U.S. Cl.
USPC ............... 435/378; 83/340; 83/342; 435/325; 435/379
(58) Field of Classification Search
USPC ................... 30/114, 306, 307, 319, 292, 301; 83/340, 342, 672
See application file for complete search history.

(56) References Cited

U.S. PATENT DOCUMENTS

| | | | |
|---|---|---|---|
| 1,557,621 A | 3/1926 | Gammeter | |
| 1,693,589 A | 12/1928 | Bolton | |
| 2,221,716 A | 11/1940 | Morton | |
| 3,472,228 A | 10/1969 | Tanner | |
| 3,776,084 A * | 12/1973 | Slyvakov | 83/342 |
| 4,068,805 A | 1/1978 | Oswald | |
| 4,292,867 A | 10/1981 | Stoffels et al. | |
| 4,302,478 A | 11/1981 | Hammann et al. | |
| 4,489,897 A | 12/1984 | Turner et al. | |
| 4,606,126 A * | 8/1986 | Davis | 30/307 |
| 4,681,001 A | 7/1987 | Uehlinger et al. | |
| 4,869,435 A | 9/1989 | Pistorius et al. | |
| 4,922,611 A | 5/1990 | Levy | |
| 5,306,279 A | 4/1994 | Atkinson | |
| 5,328,107 A | 7/1994 | Tsai | |
| 5,538,193 A | 7/1996 | Takahashi et al. | |
| 5,634,325 A | 6/1997 | Thorman et al. | |
| 5,998,129 A | 12/1999 | Schutze et al. | |
| 6,481,305 B2 | 11/2002 | Nishimura et al. | |
| 6,561,067 B2 | 5/2003 | Arrasmith | |
| 6,712,299 B2 | 3/2004 | Galletti | |
| 6,764,295 B2 | 7/2004 | Jensen et al. | |
| 6,875,607 B1 | 4/2005 | Reubinoff et al. | |
| 2002/0114788 A1 * | 8/2002 | Isacson et al. | 424/93.21 |
| 2003/0044855 A1 | 3/2003 | Anderson et al. | |
| 2004/0138686 A1 * | 7/2004 | Hsu et al. | 606/167 |
| 2004/0219668 A1 | 11/2004 | Frei et al. | |
| 2005/0106718 A1 | 5/2005 | Balasubramanian et al. | |
| 2005/0158283 A1 | 7/2005 | Zhang et al. | |
| 2005/0164383 A1 | 7/2005 | Reubinoff et al. | |
| 2005/0260747 A1 | 11/2005 | Reubinoff et al. | |
| 2006/0099192 A1 | 5/2006 | Peschel | |
| 2006/0141616 A1 | 6/2006 | Guu et al. | |
| 2007/0123888 A1 * | 5/2007 | Bleich et al. | 606/79 |

FOREIGN PATENT DOCUMENTS

| | | |
|---|---|---|
| EP | 1333085 A2 | 8/2003 |
| EP | 01344819 A2 | 9/2003 |
| JP | 2004305441 A | 11/2004 |
| WO | WO 97/29354 A1 | 8/1997 |
| WO | WO 98/14126 A1 | 4/1998 |
| WO | WO 99/23199 A1 | 5/1999 |
| WO | WO 01/22889 A1 | 4/2001 |
| WO | WO 02/098357 A2 | 12/2002 |
| WO | WO 03/020871 A3 | 3/2003 |
| WO | WO 2004/085631 A2 | 10/2004 |
| WO | WO 2004/087379 A3 | 10/2004 |
| WO | WO 2004/098285 A2 | 11/2004 |
| WO | WO 2004/099394 A2 | 11/2004 |
| WO | WO 2004/099395 A2 | 11/2004 |
| WO | WO 2005/023122 A1 | 3/2005 |
| WO | WO 2005/026811 A1 | 3/2005 |
| WO | WO 2005/038014 A1 | 4/2005 |

OTHER PUBLICATIONS

"3661pasta_cutters.jpeg," 1p., downloaded from http://fantes.com/images/3661pasta_cutters.jpeg on Dec. 11, 2005.
Buzzard, et al., "Karyotype of Human ES cells during extended culture," *Nature Biotechnology* 22(4):381-382, Apr. 2004.
Caisander, et al., "Chromosomal integrity maintained in five human embryonic stem cell lines after prolonged in vitro culture," *Chromosome Research* 14:131-137, 2006.
"Comfort Grip Roller Knife/Fork," 2p., downloaded from http://www.westons.com/acatalog/Online_Catalogue_Comfort_Grip_Rol . . . on Dec. 11, 2005.
"Creeds," 7p., downloaded from http://www.creeds.uk.com/cutting.html on Dec. 11, 2005.
"Croissant Cutter for MATFER," 3p., downloaded from http://www.instawares.com/Croissant-Cutter.MTG-141002.0.7.htm on Dec. 15, 2006.
Darnfors, et al., "High-Resolution Analysis of the Subtelomeric Regions of Human Embryonic Stem Cells," *Stem Cells* 23:483-488, 2005.
"Divider,6 Wheel Dough 1 EA," 2p., downloaded from http://www.instawares.com/Divider-6-Wheel-Dough-l-EA.JR2396.0 . . . on Dec. 12, 2005.
"Dough Docker Plastic Pins," 2p., downloaded from http://www.instawares.com/Dough-Docker-Plastic-Pins-35.DD-57 . . . on Dec. 12, 2005.
Draper, et al., "Recurrent gain of chromosomes 17q and 12 in cultured human embryonic stem cells," *Nature Biotechnology* 22(1):53-54, Jan. 2004.

(Continued)

*Primary Examiner* — Blaine Lankford
(74) *Attorney, Agent, or Firm* — Klarquist Sparkman, LLP

(57) ABSTRACT

The present disclosure provides cutting tools which include a handle coupled to a rotatable shaft having shallow grooves that extend substantially entirely across the surface of the rotatable shaft. The grooves define sharp cutting edges. In particular examples, the cutting edges are continuous, such as being defined by helical threads. The present disclosure also provides methods of dissecting a substrate of cultured cells. The substrate of cultured cells is separated into separated portions with a cutting tool. The cutting tool includes a rotatable shaft having a cutting blade which extends around the shaft. The cutting blade is rolled through the substrate to cut the substrate into portions. The portions are separated from one another to dissect the substrate.

14 Claims, 6 Drawing Sheets

(56) References Cited

OTHER PUBLICATIONS

"Fattingham Cookie Cutter," 1p., downloaded from http://pastrychef.com/Catalog/fattingham_cookie_cutter3152 . . . on Dec. 12, 2005.
"Grooved Rolling Pin," 1p., downloaded from http://www.chichissalsa.com/glossary.asp?id=36211&catitemid= on Sep. 15, 2006.
"Grooved Rolling Pin," 1p., downloaded from http://www.hormel.com/kitchen/glossary.asp?akw=&id=36211&catitemid= on Sep. 15, 2006.
"Human Embryonic Stem Cell Methods," *BresaGen Inc*. 1-19, 2004.
Mitalipova, et al., "Preserving the genetic integrity of human embryonic stem cells," *Nature Biotechnology* 23(1):19-20, Jan. 2005.
Noakksson, et al., "Monitoring Differentiation of Human Embryonic Stem Cells Using Real-Time PCR," *Stem Cells* 23:1460-1467, 2005.
"Pasta Preparation Equipment," 5p., downloaded from http://www.hormel.com/templates/knowledge/asp?catitemid . . . on Dec. 12, 2005.
"Pastry Chef Central-Baking & Pastry Tools and Equipment," 12p., downloaded from http://www.patsrychef.com/htmlpages/porducts.html on Dec. 11, 2005.
"Ribbon Cutter and Embosser Set-Wilton," 3p., downloaded from http://www.wilton.com/store/site/product.cfm?id=BA23EDC2-802D . . . on Dec. 13, 2005.
Richards, et al., "Human feeders support prolonged undifferentiated growth of human inner cell masses and embryonic stem cells," *Nature Biotechnology* 20:933-936, Sep. 2002.
"Roll Easy Lotion Applicator," 3p., downloaded from http://www.elderstore.com/roll-easy-lotion-applicator.aspx on Dec. 16, 2005.
"Roller Hand Cutter," 1p., downloaded from http://www.italianhomecooking.com/cgi-bin/storepro.php on Dec. 12, 2005.
"Rolling Pin Texture Tools," 2p., downloaded from http://www.continentalclay.com/Product.aspx?ProductId=619&Category...on Dec. 13, 2005.
"Roling Pin-Wood-18 inch-Ravoili," 1p., downloaded from http://www.italianhomecooking.com/cgi-bin/online/storepro.php on Dec. 12, 2005.
"SmarterKids," 1p., downloaded from http://www.smarterkids.com/product/product.asp?sku=1031&redir=true on Dec. 13, 2005.
"Stem Cell Cutting Tools," 1p., downloaded from http://www.swemed.com/shop/custom/dept.aspx?groupid=41477&sort . . . On Sep. 14, 2006.
"Textured Rolling Pins for Use with Fondant Icing," 6p., downloaded from http://www.sugarcraft.com/catalog/gumpaste/FMM/rollingpins.htm on Dec. 13, 2005.

* cited by examiner

DISSECTION TOOL AND METHODS OF USE

TECHNICAL FIELD

The present application relates generally to dissection tools and their methods of use. In particular examples, the present disclosure relates to dissection tools that include a rolling blade and that may be used to separate cells in culture.

BACKGROUND

Cells are cultured by seeding them into a culture dish, where the cells experience a recovery phase after being removed from their primary environment. Eventually, the cells settle and undergo exponential growth until they approach confluency, at which point contact inhibition occurs and the cells enter a plateau stage of growth. In order for cells to grow beyond confluency they generally must be passaged (separated). Passaging may be performed, for example, by dividing the cells into multiple culture containers at a known concentration and adding fresh media to the containers.

Human embryonic stem cells are examples of cultured cells that are valuable both for research and therapeutic purposes. These cells, harvested from the inner cell mass of an early embryo, can proliferate indefinitely while retaining the ability to give rise to any part of the body. However, cell cultivation generally requires that the cultured stem cells be passaged into separate portions using mechanical, enzymatic or chemical methods. The separated portions of the cell colony are then used to seed cultures and establish new colonies of stem cells, often in viscous or gel-like media. There are advantages and disadvantages to using either mechanical dissection or chemical/enzymatic methods.

Some studies indicate that manual passaging better preserves the karyotype of the stem cells. Conventional techniques for manually dissecting a cell colony involve cutting the cell colony with the edge of a sharp object, such as the broken tip of a glass pipette. A commercial version of this device, the Stem Cell Cutting Tool, is available from Swemed Lab International AB of Billdal, Sweden. However, manual dissection can be time consuming because bulk passaging is typically not possible using physical dissection. Numerous individual cuts are therefore typically needed to dissect a cell colony. In addition, physical dissection can result in cell colony portions having non-homogenous sizes or shapes. In contrast, while enzymatic digestion allows for bulk passaging, it is typically more likely to induce chromosomal changes in the cells.

U.S. Published Application 2004/0138686 (the '686 Publication) purports to describe a tool that can be used to cut a cell colony into multiple pieces with one pass of the tool. Specifically, this publication describes a tool having a handle and an incision knife module having multiple fixed or rolling blades. However, this tool may suffer from a number of disadvantages. For example, the tool may not only cut the cell colony, but an underlying surface, such as a plate. If the underlying surface is cut, it can be difficult to dislodge and harvest the cut cell colony pieces. Also, when cutting the cell colony, parts of the colony may be pushed into the spaces between the knife blades. If this occurs, the tool may have reduced cutting efficiency and may damage the cell colony, as well as cells crushed in the spaces between the knife blades. Accumulation of material between the blades may require more frequent cleaning or make the tool more difficult to clean.

The tools disclosed in the '686 Publication appear to have relatively narrow cutting widths, such as 1 cm or less. If the substrate to be cut is relatively large, a greater number of cutting passes are likely to be required, increasing the time needed to dissect the colony, potentially decreasing cut homogeneity, and possibly leading to increased fouling of device. Additionally, the small size of the device may make it difficult to construct, assemble, or disassemble.

SUMMARY

The present disclosure provides dissection tools that may be used to cut a substrate, such as a cell colony, into multiple portions. The dissection tools include a handle and a rotatable shaft coupled to the handle for rotation about a rolling axis. In particular examples, the handle is bent or flexible. Shallow grooves in the surface of the rotatable shaft define sharp cutting edges that in some embodiments extend substantially entirely across the surface of the rotatable shaft. In particular examples the grooves are continuous, for example extending helically around the rotatable shaft. A user may cut a substrate, such as a substrate of cultured cells, into multiple portions by rolling the rotatable shaft over the substrate, thus cutting the substrate with the grooves of the rotatable shaft.

The present disclosure provides methods of dissecting a substrate of cultured cells. According to one such method, the substrate of cultured cells is separated into separated portions with a cutting tool. The cutting tool includes a rotatable shaft having a cutting blade that extends around the shaft, for example the cutting blade described herein. The cutting blade is rolled through the substrate to cut the substrate into portions. The portions are separated from one another to dissect the substrate.

In particular examples, the substrate for cultured cells is a first substrate and the method includes transferring stem cells to the first substrate. The first substrate is incubated until the stem cells form colonies having a cross section, for example of at least about 1 mm. After dissecting the cells with the cutting tool, the portions obtained by dissection are transferred to a second substrate that includes culture medium. The second substrate is then incubated.

There are additional features and advantages of the subject matter described herein that will become apparent as this specification proceeds.

In this regard, it is to be understood that this is a brief summary of several aspects of the subject matter described herein. The various features described in this section and below for various embodiments may be used in combination or separately. Any particular embodiment need not provide all features noted above, nor solve any particular set of problems in the prior art noted above.

BRIEF DESCRIPTION OF THE DRAWINGS

Various embodiments are shown and described in connection with the following drawings in which.

DETAILED DESCRIPTION

In order to facilitate review of the various embodiments of the disclosure, the following explanations of specific abbreviations are provided:
bFGF—heparin binding growth factor
CKSR—conditioned knockout serum replacement
CMEF—complete mouse embryonic fibroblast medium
DMEM—Dulbecco's modified Eagle's medium
EDTA—ethylenediaminetetraacetic acid
FBS—fetal bovine serum
hESC—human embryonic stem cell
KSR—knockout serum replacement
MEF—mouse embryonic fibroblast Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together. Although methods and materials similar or equivalent to those described herein can be used in the practice or testing of the present disclosure, suitable methods and materials are described herein. The disclosed materials, methods, and examples are illustrative only and not intended to be limiting.

Figure 1:
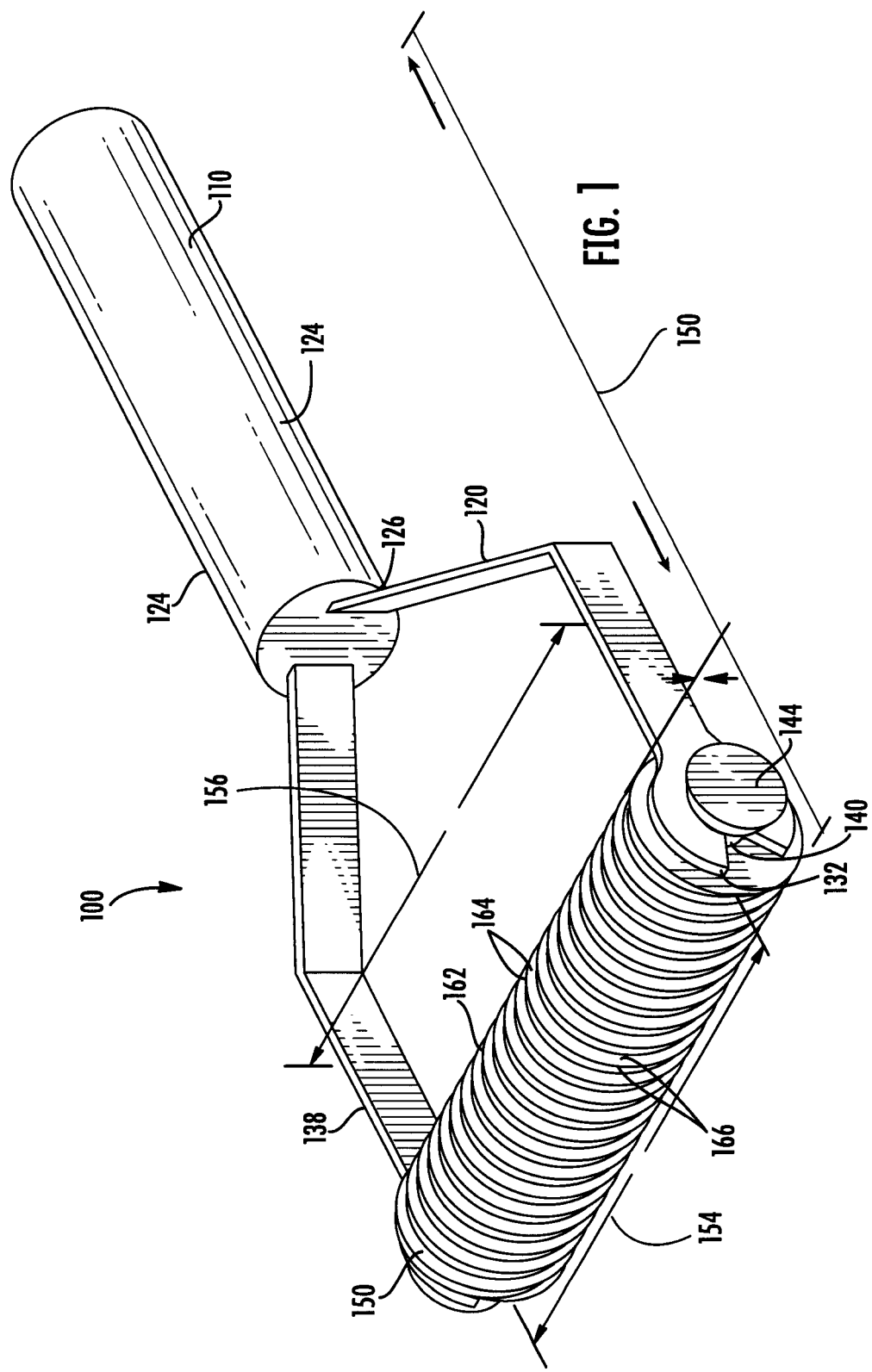
FIG. 1 is a top perspective view of a dissection tool according to the present disclosure.

FIG. 1 illustrates a dissection tool 100 according to an aspect of the present disclosure. The tool 100 includes a handle 110 from which a fork 120 extends. The handle 110 is illustrated as a cylinder having a circular cross section. However, the handle 110 may be shaped differently. For example, in some implementations, the handle 110 has another arcuate cross section (such as parabolic, elliptical or semicircular cross section) or a rectangular cross section (such as a square). The handle 110 is shown as being straight, but is bent or arcuate in further implementations. In a particular example, the fork 120 is bent at a 15 degree angle relative to the handle 110.

The handle 110 may be constructed from any suitable material, such as metals or plastics. In a particular example the handle 110 is made of stainless steel. The handle 110 may be coated with one or more coatings, such as a rubber coating to provide a gripping surface with enhanced frictional characteristics. The handle 110 may be rigid or flexible. In some examples, the handle 110 includes at least one rigid portion and at least one flexible portion. In a particular example, the handle 110 includes two rigid portions separated by a flexible portion. In a more specific example, a flexible portion is disposed intermediate the handle 110 and the fork 120. The flexible portion may be constructed from a flexible material, such as plastic or rubber, or may be constructed to flex, such as having an accordion structure.

In FIG. 1, the fork 120 is shown extending from opposing lateral sides 124 of the proximal end 126 of the handle 110. The fork 120 may be integral with the handle 110 or may be a separate component coupled to the handle 110. For example, the fork 120 may be coupled to the handle 110 by welding, pressure fit, friction fit, mechanical joint, or through the use of an adhesive. In one example, mounting apertures (not shown) are formed in the lateral sides 124 of the handle 110, close to the proximal end 126 of the handle 110. The proximal ends of the fork 120 include laterally extending projections (not shown) that can be inserted through the mounting apertures. In another example, the proximal end of the fork 120 forms a slightly flexible loop (not shown) that can be inserted into the open (hollow) proximal end 126 of the handle 110 and retained in position by a pressure and friction fit. The fork 120 may be constructed from the same types of materials as the handle 110, which may be the same as or different than the materials used to construct the handle 110.

In a further implementation, mounting arms 138 of the fork 120 extend from a shaft (not shown) that is attached to the handle 110. The shaft may be permanently or releasably attached to the handle 110. In a particular example, the handle 110 includes an outwardly biased projection extending from a section near its proximal end 126. The end of the shaft includes a cavity (not shown) configured to fit over the handle 110 and an aperture (not shown) configured to receive the outwardly biased projection when the shaft is coupled to the handle 110. In other examples, the proximal end 126 of the handle 110 is hollow and includes an aperture (not shown) for receiving an outwardly biased projection (not shown) of the shaft when the shaft is inserted into the handle 110. In either example, the handle 110 can be removed from the fork 120 by depressing the outwardly biased projection through the aperture and sliding the fork 120 away from the handle 110.

The distal ends 132 of the fork 120 are coupled to a shaft 140 that provides a cylindrical rolling blade 150. The shaft 140 may be coupled to the fork 120 by any suitable means. As shown in FIG. 1, the distal ends 132 of the fork 120 include arcuate slots. The axial ends of the shaft 140 extend through the slots which are sized to fit around the shaft 140 and rotatably connect it to the handle 110.

A retention plate 144, which is formed on the axial ends of the shaft, is seated externally to distal ends 132 of fork 120 to help retain the shaft 140 on the fork 120. Other means can be used to retain the shaft 140 on the fork 120. For example, the ends of the shaft 140 may include apertures (not shown) through which retaining pins (not shown) may be placed. In another example, the ends of the shaft 140 are threaded and retaining nuts (not shown) may be screwed onto the threads. Alternatively, the ends 132 of the fork 120 can include pins insertable into apertures on the shaft 140.

The shaft 140 may be coupled to the fork 120 using other connectors. In one example, rather than the slots 134, the distal fork ends 132 define opposing cavities (not shown) on their inner faces. The ends of the shaft 140 are complementary to the shape of the cavities, and are cooperatively received in the cavities for retention to the handle. In embodiments wherein the shaft 140 is removable, the fork 120 may be sufficiently flexible to permit the ends of the shaft 140 to be removed from the cavities in the distal fork ends 132. In a further implementation, the shaft 140 is compressible, for example with an internal spring, to allow the shaft 140 to be compressed and the ends removed from the cavities.

In particular implementations, including that shown in FIG. 1, the shaft 140 is removable from the fork 120. The distal fork ends 132 or shaft 140 are, in some implementations, made from a flexible material, such as rubber or plastic. The use of a flexible material can aid in inserting and removing the shaft 140 from openings in slots formed in the distal fork ends 132.

The rolling blade 150 may be integral with the shaft 140 or may be a separate component, such as being coupled to the shaft 140. When the rolling blade 150 and shaft 140 are integral, the blade 150 may be formed in the external surface of the shaft 140. When the rolling blade 150 and shaft 140 are separate, the rolling blade 150 may be a sleeve or otherwise have an axial cavity through which the shaft 140 passes. Connectors (such as pins) can extend from shaft 140 to engage rolling blade 150 so that it rotates with shaft 140.

Although FIG. 1 illustrates the tool 100 with a relatively short handle 110 in order to accentuate the features of the rolling blade 150, the tool 100 may be made in any desired dimensions. In a particular implementation, the tool 100 has a length 150 of about 15 cm, such as having a handle 110 with a 10 cm axial length, and a 5 cm distance between the fork 120 and the outer edge of the rolling blade 150. The width 154 of the rolling blade 150 is, in some examples, between about 5 mm and about 5 cm. In further examples, the width 154 is at least about 2 cm. The maximum width 156 of the fork 120, such as from rim 144 to rim 144 between which the shaft 140 is carried, is about 8 mm in a particular example.

The rolling blade 150 presents a plurality of cutting edges 162. The cutting edges 162 may be formed from any suitable structure, and may be aligned (for example in parallel). In one example, the cutting edges 162 are formed from a series of blades or formed by the crests of channels formed in the rolling blade 150. As shown in FIG. 1, the cutting edges 162 are formed from threads 164 in the surface of the rolling blade 150. The illustrated cutting edges 162 are the crests of the threads 164. Although FIG. 1 illustrates helical cutting edges 162, the cutting edges 162 may be disposed in other patterns, including as a series of axially aligned, parallel and non-continuous circular cutting edges 162. In some examples, the cutting edges 162 form a continuous cutting edge, such as when the rolling blade 150 is helically threaded. In other examples, the cutting edges 162 are part of discrete cutting members disposed about the rolling blade 150 in a non-continuous arrangement.

The rolling blade 150 may be constructed from any suitably rigid material, such as metals and plastics. In one example, the rolling blade 150 is made of stainless steel. The cutting edges 162 can be made from the same material as the rolling blade 150 or from a different material. In one example, the dissection tool 100 has a plastic rolling blade 150 with metal cutting edges 162. The material from which the rolling blade 150 is constructed may be selected to be sterilizable, such as in an autoclave. The rolling blade 150 may therefore in some embodiments be substantially sterile (free from contaminating microorganisms that could be inoculated into the culture medium). In some embodiments, the rolling blade 150 is constructed from a material that will not damage a surface on which a substrate is placed. For example, the material may be selected to be firm enough to cut a cell colony, but sufficiently soft or flexible to avoid damaging a plate on which the cells are placed. Plastic rolling blades 150 may be used in some such embodiments.

Figure 2:
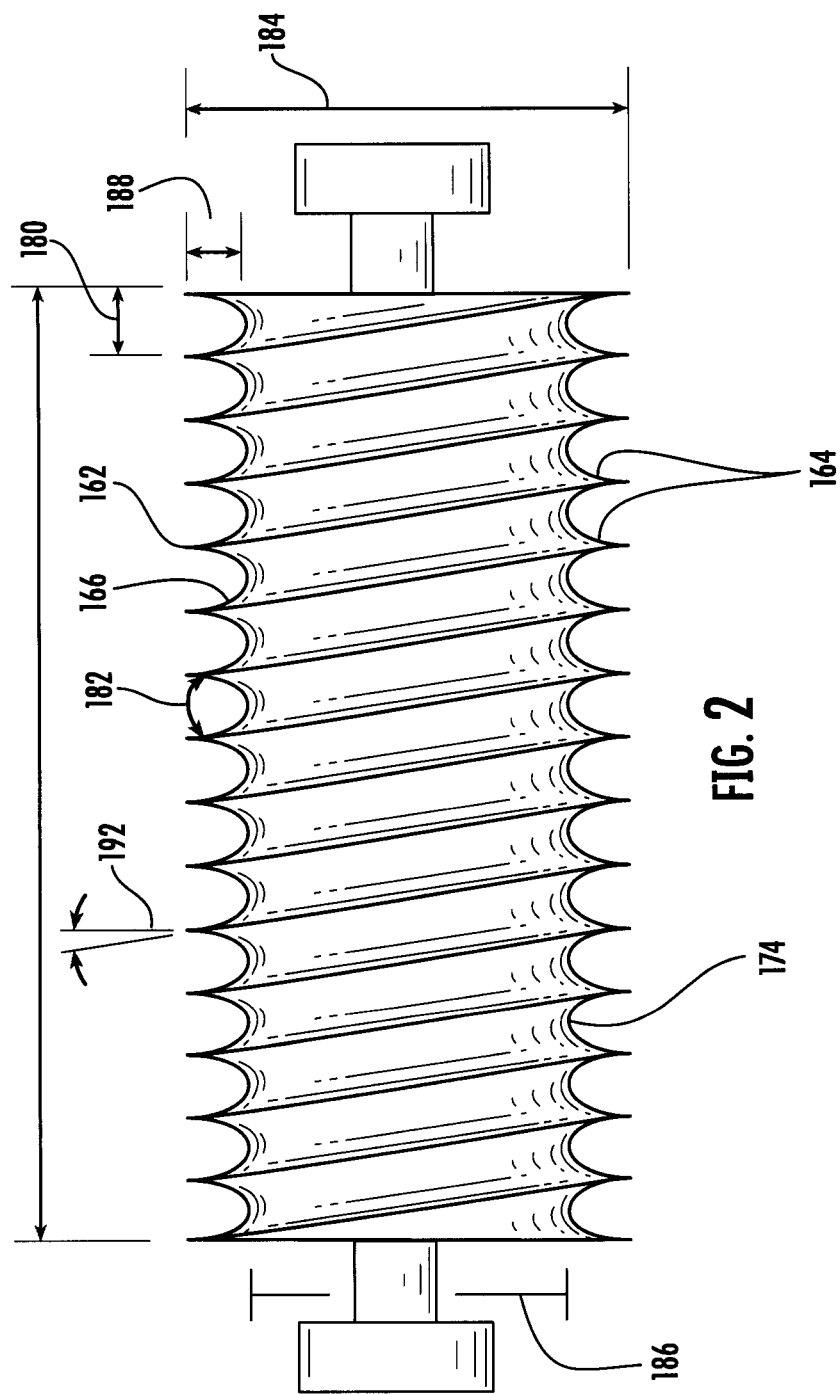
FIG. 2 is an enlarged front view of the rotatable shaft of the dissection tool of FIG. 1.

FIG. 2 illustrates a detailed enlarged front view of the rolling blade 150 and shaft 140 of FIG. 1. The cutting edges 162 may be continuous (for example extending in a helix around the shaft) or discrete (parallel). The dimensions of the cutting edges 156 may be varied depending on the particular application. The following discussion provides examples of suitable cutting edge 162 dimensions for cutting embryonic stem cell colonies and embryoid bodies. Although described in terms for helical threads, similar dimensions can be used for non-helical or discrete cutting edges 162.

In particular examples, the cutting edges 162 are the crests of the threads 164, which have roots 174. The thread pitch 180, or distance between the crests of adjacent threads 164, is in certain examples between about 150 µm and about 1000 µm. For example, when the tool 100 will be used to cut stem cell colonies, it may be beneficial for the thread pitch 180 to be between about 150 µm and 300 µm. When the tool 100 will be used to cut embryoid bodies, it may be beneficial for the thread pitch 180 to be between about 500 µm and 1000 µm. Of course, larger or smaller thread spacings can be used in particular implementations, if desired.

The angle between adjacent cutting edges 162, the thread angle 182, can be varied as desired. In some examples, the thread angle 182 is between about 40° and about 60°. Larger thread angles 182 may help reduce the accumulation of material between the cutting edges 162 when the tool 100 is used to cut through a substrate. The flanks 166 of the cutting edges 162 are straight, convexly curved, or concavely curved in various examples and each flank 166 may have the same or different sides. In a particular example, all of the flanks 166 of the cutting edges 162 are concavely curved. Individual threads 164 can extend vertically, perpendicularly to the thread axis, or can have a rake angle.

The radial dimensions of the shaft 140, the rolling blade 150, and the cutting edges 162 can be varied as desired to produce a particular cutting effect. In particular examples the major thread diameter 184, the distance between the center of the shaft 140 and the crests 162 of the threads 164, is between about 2 mm and about 5 mm. The minor thread diameter 186, the distance between the center of the shaft 140 and the roots 174 of the threads 164 is chosen to provide a thread height 188 (the distance between the roots 174 and crests 162 of the threads 164) of at least about 0.2 mm. The thread height 188 is typically chosen to be sufficiently large to penetrate a substrate to be cut. In some implementations, it may be desirable to minimize the thread height 188 in order to provide threads 164 with relatively shallow grooves in order to help reduce the potential for substrate to accumulate in the grooves.

The crests 162 come to a point in particular examples. In further examples, the crests 162 have a width that extends between each flank 166. The crest width, in particular examples, is less than about 2 µm. In some implementations, the crest width is flat, that is, parallel to the axis of the shaft 140. In further implementations, the crest width is rounded, such as having a convex or concave curvature. Similarly, the roots 174 of the threads 164 are pointed in some examples, and include a root width in further configurations. When the roots 174 include a width, the width is flat or curved, as desired. In a particular example, the crests 162 are sharp and the roots 174 include a flat root width.

The lead angle 192, the angle of the threads with respect to a plane perpendicular to the thread axis (the axis of the shaft 140), is typically chosen to provide a desired rolling action of the tool 100. Typically, the larger the lead angle 192, the more the tool 100 will roll at an angle. Smaller lead angles 192 may result in tools 100 that are easier to use. In particular examples, the lead angle 192 is less than about 15°, such as less than about 5°.

The cutting edges 162 may have a number of shapes. For example, both flanks 166 of a cutting edge 162 may be curved. The curve of each side 166 may be the same or different and may be varied to provide a desired cut. The curve can be convex or concave. In further implementations, one side 166 of the cutting edge 162 is curved and the other side 166 is parallel to the radius of the rolling blade 150. In yet further configurations, both flanks 166 of the cutting edges 162 are parallel to the radius of the rolling blade 150.

The height, shape, spacing, pitch, and other properties of the cutting edges 162 may be varied to provide a particular type of cut, such as particular sharpness, depth, or cut spacing.

In a particular example, the cutting edges 162 are spaced together sufficiently closely such that a substrate will not be damaged by rolling action of smooth (non-cutting edge) surfaces of the rolling blade 150 over the substrate. The properties of the cutting edges 162 may be selected based on the material to be cut. For example, the softness, surface resistance, moisture content, and thickness of a particular substrate may affect the cut provided by a particular cutting edge 162.

Figure 3:
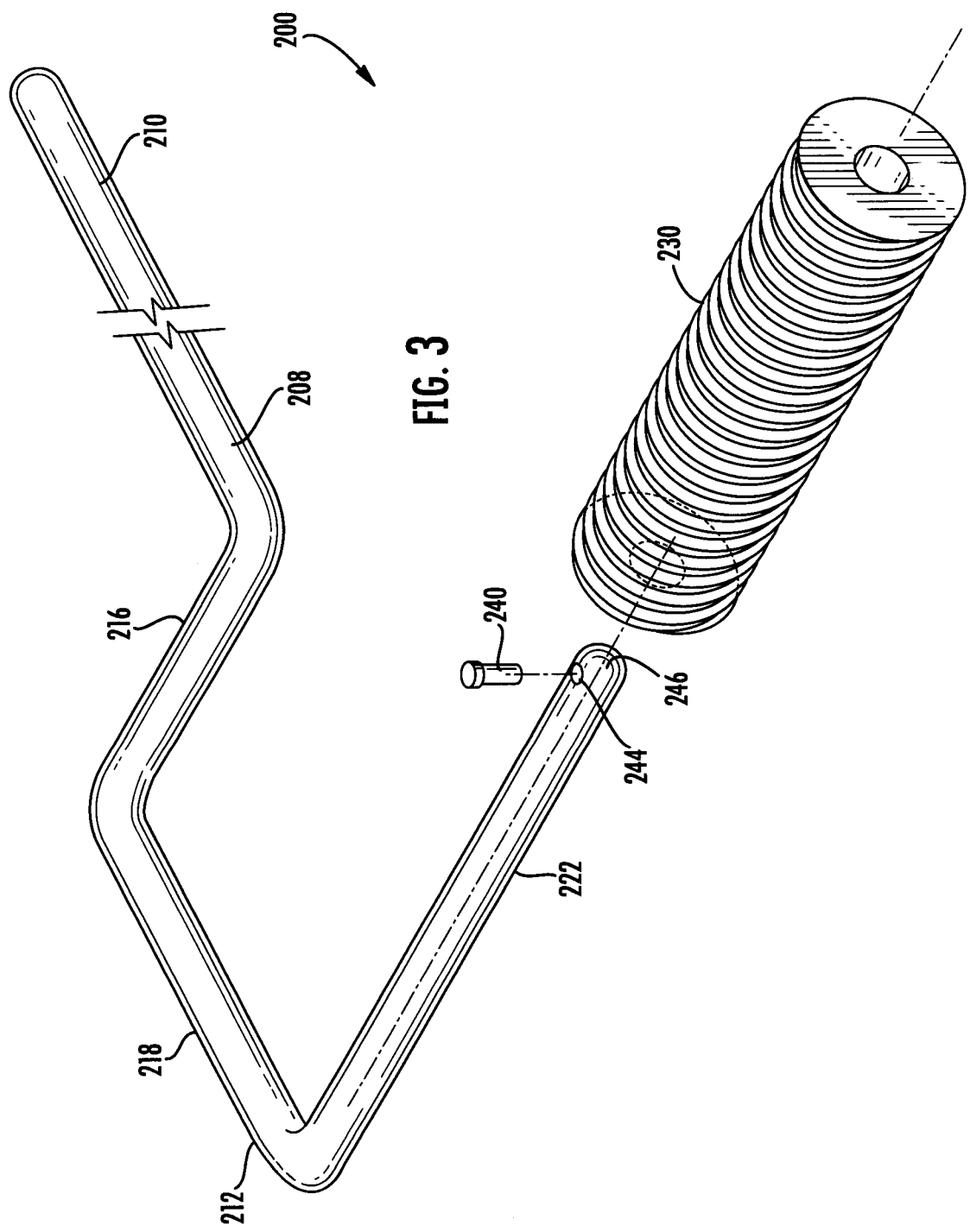
FIG. 3 is a perspective view of another dissection tool according to the present disclosure.

FIG. 3 illustrates a dissection tool 200 according to a further embodiment of the present disclosure. The dissection tool 200 includes a handle 208 having a gripping end 210 and a working end 212. The working end 212 is generally U-shaped, having a short transverse side 216, a longitudinal connecting portion 218, and a transverse mounting section 222. The gripping end 210 is generally aligned with the center (midpoint) of the transverse mounting section 222.

A rolling blade 230 is positionable on the transverse mounting section 222. The rolling blade 230 may be designed as described above for the rolling blade 150 of FIG. 1. The rolling blade 230 can be retained on the transverse mounting section 222 as described above for retaining the shaft 140 (FIG. 1) to the fork 120 (FIG. 1). For example, a pin 240 may be inserted through an aperture 244 formed in the distal end 246 of the transverse mounting section 222. In another example, the distal end 246 of the transverse mounting section 222 is threaded and a retainer (not shown), such as a nut, is threadable onto the distal end 246.

Figure 4:
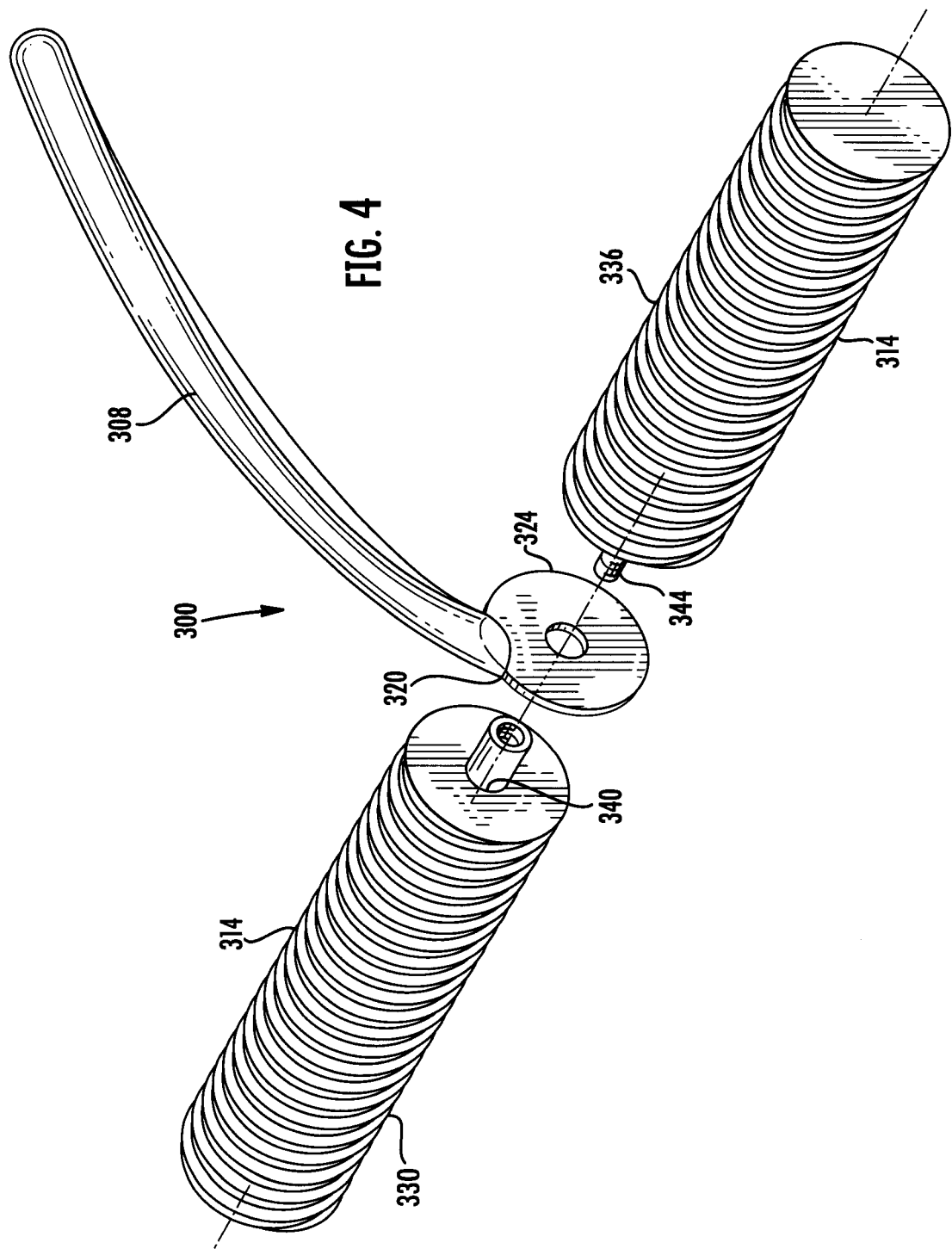
FIG. 4 is a perspective view of a further disclosed dissection tool.

A dissecting tool 300 is illustrated in FIG. 4. The dissecting tool 300 includes a handle 308 aligned with the midpoint of a rolling blade 314. The handle 308 and rolling blade 314 may be designed in an analogous manner to the handle 110 and rolling blade 150 shown in FIG. 1. The proximal end 320 of the handle 308 includes a blade mount 324. The blade mount 324 is a circular structure through which the rolling blade 314 extends. In a particular implementation, the rolling blade 314 includes mating first and second sections 330, 336. Each section 330, 336 includes a coupler 340, 344, such as a threaded aperture or a matingly threaded shaft, extending axially from an end of the respective section 330, 336. The first and section sections 330, 336 can be coupled through the blade mount 324.

In further implementations, the blade mount 324 is a solid structure having cavities into which pins (not shown) from the first and second sections 330, 336 can extend. In an alternative embodiment, the blade mount 324 includes the pins which extend into apertures formed in first and second sections 330, 336. The blade mount 324 or the blade 314 can include additional components to facilitate rotation of the rolling blade 314, such as ball bearings. For example, a race of ball bearings can be included in the blade mount 324.

Figure 5:
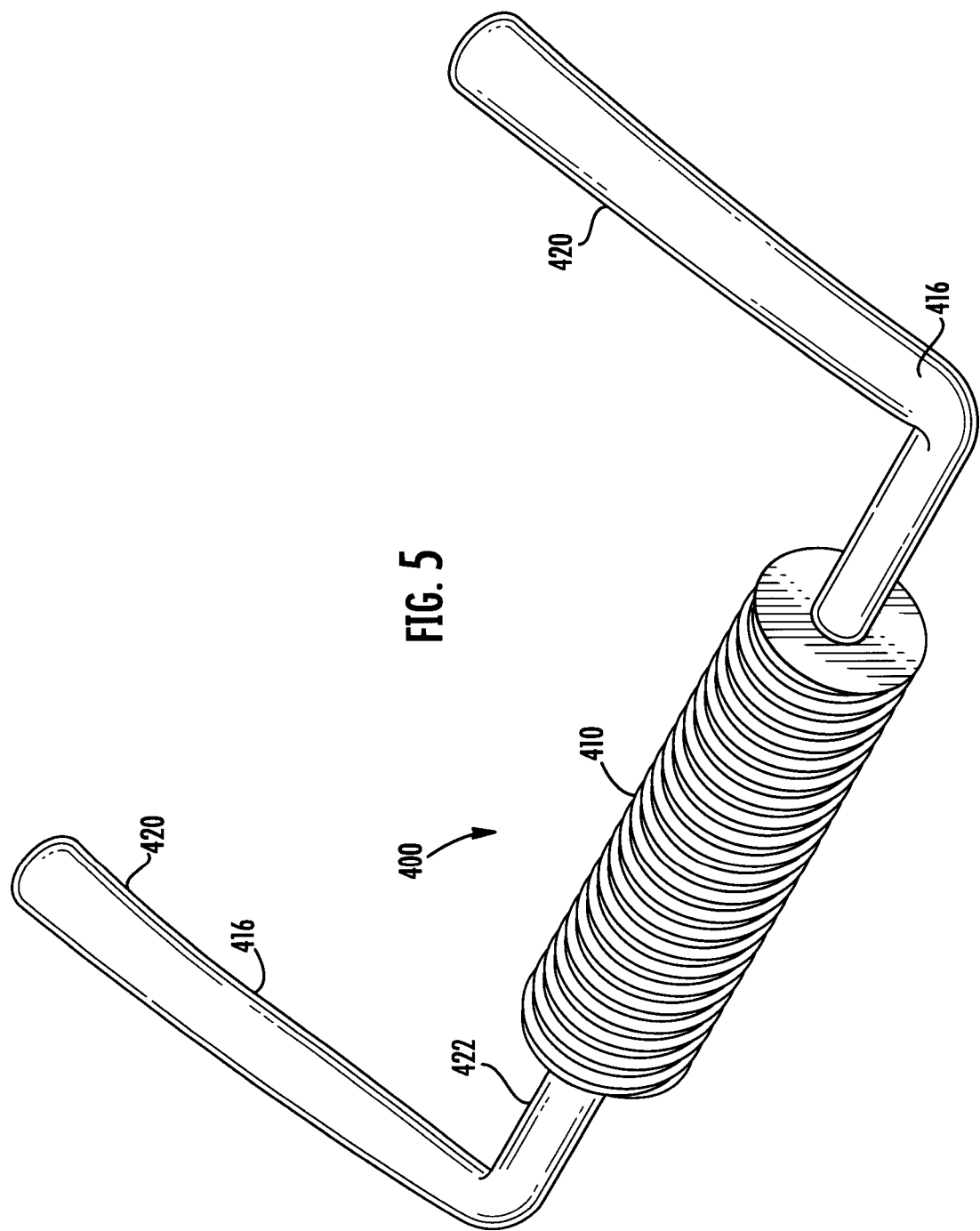
FIG. 5 is a perspective view of a yet further dissection tool according to the present disclosure.

FIG. 5 illustrates a dissecting tool 400 according to the present disclosure. The dissecting tool includes a rolling blade 410. Handles 416 extend axially from each end of the rolling blade 410. The handles 416 are bent and distal ends 420 extend perpendicularly to the axis of the rolling blade 410 and proximal ends 422 of the handles 416. In alternative implements, the handles 416 extend axially outwardly from the rolling blade 410 and are not bent. In yet further implementations, the handles are bent at an angle other than 90 degrees.

The rolling blade 410 may be connected to the handles 416 in any suitable manner. For example, the handles 416 may be extensions of a shaft (not shown) over which the rolling blade 410 is positioned. Alternatively, the handles 416 or rolling blade 410 include pins (not shown) and the other component includes apertures (not shown) into which the pins pass. The rolling blade 410, in some implementations, includes bearings (not shown) or other components to help facilitate rotation of the rolling blade 410.

The above disclosed dissection tools may be used by passing the rotatable shaft of the dissection tool over a substrate, such as a substrate of cultured cells. In some examples, the cultured cells are embryonic stem cell colonies or embryoid bodies. The tool is grasped by a handle, the cutting edges placed in frictional contact with the substrate, and the tool advanced over the substrate in a first direction to cut the substrate into portions, such as slices. The rolling blade is then passed over the substrate in a pathway that intersects the first pathway to subdivide the portions into sub-portions. In a particular example, the second pathway is perpendicular to the first pathway, and the sub-portions are rectangular. The sub-portions are then separated from one another to dissect the substrate.

The separated portions or sub-portions are, in some examples, transferred to a container, such as a container that includes culture medium. The container can be treated, such as by incubation, to promote the growth of the portions or sub-portions. In further examples, the container can be treated to preserve the portions or sub-portions, such as by freezing the container.

In particular implementations, the disclosed cutting tools are used in methods of passaging cells, such as embryonic stem cells. A desired cell source is obtained and cultured to a desired stage of growth. For example, the cells may be grown to confluency, the point at which the concentration of cells prohibits further growth. In other examples, the cells may be grown until an aggregate of cells, such as a cell colony reaches a certain size, such as at least about 1 mm in cross section. The cell aggregate, or confluent cell mass, is then passaged using a disclosed dissection tool and the resulting dissected portions can be used, grown, and stored as desired.

Figure 6:
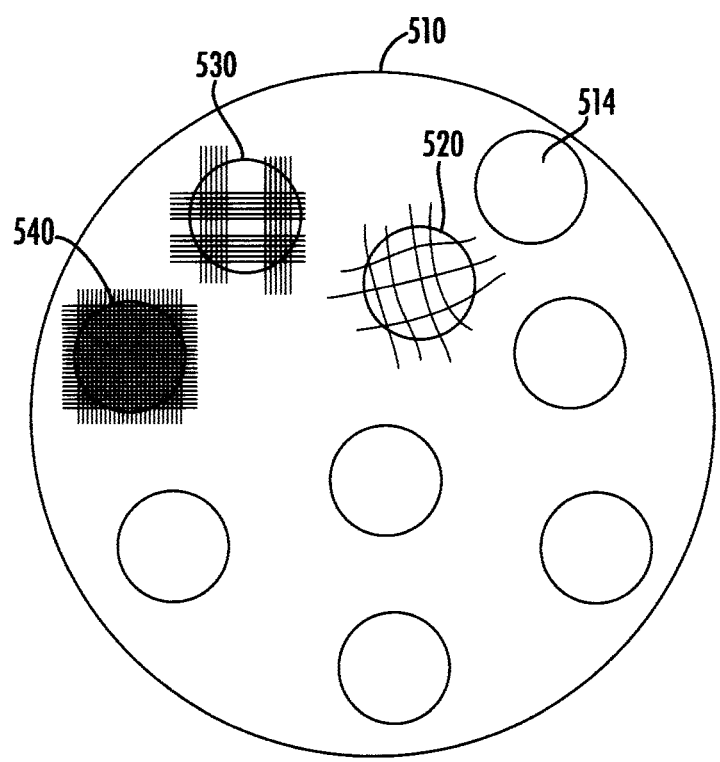
FIG. 6 is a schematic illustration of some cell colonies substrate being cut into portions using the disclosed dissection tool, and other colonies subdivided with another dissection technique.

FIG. 6 schematically illustrates a plate 510 having a plurality of cell colonies 514. Colony 520 was cut using manual dissection, such as with the broken tip of a glass pipette. The colony pieces have irregular shapes and sizes. Colony 530 was cut using a cutting tool having a relatively narrow cutting width. Multiple passes of the tool are required to completely cut the colony 530. Colony 540 was cut using implementations of the disclosed dissection tools having a cutting surface at least substantially the same width as the diameter of the cell colony 540. Only two passes of the dissection tool in substantially perpendicular directions completely cut the cell colony 540 and the majority of pieces are at least substantially the same size and shape.

Embodiments of the disclosed dissection tools may provide a number of benefits. For example, the disclosed tools may allow a number of cuts to be made with one pass of the tool. Two passes of the tool can cut a substrate into a large number of sub-portions. The process of cutting a substrate, such as a colony of stem cells, can be faster than previous manual methods. In addition to being more efficient, disclosed tools may allow for more uniform portions or sub-portions to be cut because of the regular spacing of the cutting surfaces on the rotatable shaft and the relatively small number of cuts needed.

Unlike some prior cutting tools, at least certain disclosed dissection tools employ rotatable shafts that help prevent accumulation of material between cutting surfaces. For example, the disclosed dissection tools may use closely spaced blades, reducing the amount of empty space into which material can pass. Embodiments in which the grooves are connected by sharp edges or blades may reduce damage to the substrate, such damage caused by the pressure of smooth (non-cutting) surfaces of the rotatable shaft on the substrate. The dissection tools can also be formed with relatively shallow grooves between adjacent blades, also reducing the amount of space into which material can pass.

Certain embodiments of the disclosed dissection tools have easily changeable rolling blades. Easily changeable blades can allow soiled cutting surfaces to be easily replaced with clean cutting surfaces. In particular, disposable blades can be particularly useful in avoiding contamination of a substrate with material on a blade leftover from previous uses. As described above, rotatable shafts can be designed with different properties, such having different blade materials (such as a plastic blade instead of a metal blade), cutting edge material, cutting edge spacing, cutting edge depth, cutting edge orientation, and cutting edge shape. Interchangeable rotatable shafts allow a user to use a single dissection tool with a plurality of rolling blades. The user can thus select a suitable blade to be used with material to be cut, or change blades based on the initial results of a cutting blade.

In particular embodiments, the present disclosure provides a kit which includes a dissection tool base (the portion of the dissection tool other than the rotatable shaft) and at least two rolling rotatable shafts. The rolling blades may be the same or different.

Various embodiments are specifically illustrated by the following example.

EXAMPLE

Cultivation and Passaging of Human Embryonic Stem Cells

A desired human HESC cell line is obtained from a suitable source, such as BresaGen, Inc., of Athens, Ga. The cell line is maintained on mouse embryonic fibroblasts (MEF) according to the suppliers' protocols. In one example, the MEFs are maintained in 20% Knockout Serum Replacement (KSR) hESC medium. The KSR hESC medium is prepared from Dulbecco's modified Eagle's medium with F-12 nutrient mix (DMEM:F12, Invitrogen), 20% KSR (Invitrogen), 4 ng/ml heparin binding growth factor (bFGF, Invitrogen), 2 mM glutamine (Invitrogen), 0.1 mM non-essential amino acids (Invitrogen), 50 U/mL penicillin and 50 µg/ml streptomycin (Invitrogen), and 0.1 mM β-mercaptoethanol (Invitrogen).

If desired, the KSR hESC medium can be conditioned with MEFs prior to use to provide a conditioned KSR (CKSR) HESC medium. In such cases, $4\times10^6$ MEFs (StemCell Technologies, Inc., Vancouver, Calif., or Specialty Media of Phillipsburg, N.J.) treated with mitomycin C (A.G. Scientific, Inc., San Diego, Calif.) are plated in a T75 flask coated with 0.5% gelatin. If desired, MEFs can be prepared rather than purchased. A suitable protocol for preparing MEFs is described in the BresaGen 2004 HESC Methods Manual, v2.1, available at http://stemcells.nih.gov/staticresources/research/protocols/BresaGen_hESC_manual_2.1.pdf.

The flask contains complete MEF (CMEF) medium. The CMEF medium is prepared from DMEM with high glucose (Invitrogen), 10% fetal bovine serum (FBS, Invitrogen), 0.1 mM non-essential amino acids (Invitrogen), and 50 U/ml penicillin and 50 µg/ml streptomycin (Invitrogen). After 1 day, the CMEF medium is removed and replaced with 37.5 ml of the 20% KSR HESC medium that contains 4 ng/ml bFGF. The flask is incubated for 24 hours at 37° C. and 5% $CO_2$.

The conditioned KSR HESC medium is removed from the flask and sterilized with a 0.22 µM filter. This procedure can be repeated with additional aliquots of KSR hESC for up to seven days. Before use, the concentration of 1-glutamine is adjusted to 2 mM and the bFGF concentration is adjusted to 4 ng/ml in the CKSR hESC medium. The concentration of β-mercaptoethanol is adjusted daily to 0.1 mM using freshly thawed β-mercaptoethanol.

The appropriate number of vials of MEFs are thawed for plating. For a 100 mm dish, about $1.2\times10^7$ cells are plated. The dish is typically not gelatin coated, but may be, if desired. Thawing is accomplished by placing the vial in a 37° C. water bath and gently shaking the vial by hand. In a laminar flow cabinet, the cells are transferred to a 50 ml conical tube. 10 mL of CMEF medium is added dropwise with swirling. Another 10 ml of CMEF is then added and the tube is then centrifuged for 4 minutes at 200 g.

The cells are resuspended in 50 ml of CMEF. Viable cells are counted using trypan blue exclusion and typically exceed 95%. The cells are plated into T175 flasks at $2.5\times10^6$ cells per flask. About 30 ml of medium is in each flask. The flasks are then incubated for 37° C. at 5% $CO_2$.

After three days, the cells are at about 90-95% confluency. Each flask is checked microscopically to confirm cell growth and sterility. The medium from each flask is aspirated and the cells treated with 16 mL 10 µg/ml mitomycin C in CMEF media for 2.5 hours at 37° C. and 5% $CO_2$. The mitomycin C solution is aspirated and the cells washed.

The cells are first washed with 20 ml $Ca^{2+}/Mg^{2+}$-free phosphate buffered saline (PBS) by laying the flasks on their sides and gently rocking them. The PBS is then aspirated. To the flask is added 3 ml of 0.05% trypsin/EDTA (Invitrogen), which is then dispersed in the flask by tipping and tapping the flask. After a minute or two, the cells detach from the flask and 5 ml of the CMEF medium is added to the flask. The medium in the flask is rinsed over the sides of the flask several times to wash off any adherent cells. The cell suspensions from up to 6 flasks are then pooled in a 50 ml conical tube. The flasks are rinsed with 10 ml CMEF and the contents added to the conical tubes to a total volume per tube of 50 ml.

The conical tubes are centrifuged for 4 minutes at 200 g. The medium is aspirated and the cells are pooled and then resuspended in 10 ml CMEF. The conical tubes are rinsed with 10 ml CMEF medium, which is added to the pooled tubes to bring the total volume of each tube to 50 ml. The tubes are then centrifuged for 4 minutes at 200 g. The medium is aspirated and the cells resuspended in 10 ml CMEF. CMEF is added to each tube to a total volume of 50 ml. The cells are then centrifuged at 200 g for 4 minutes. The cells are then again aspirated, diluted with CMEF to a total volume of 50 ml, and centrifuged as before.

The tubes are aspirated and the cells resuspended in CMEF medium. The cells are counted using trypan blue exclusion. If too concentrated, the cells can be diluted to allow their concentration to be measured. Once the cell count has been performed, the cells are diluted to a desired concentration with CMEF and then plated out to generate the inactivated MEF feeder layers. The plates are cultured at 37° C. and 5% $CO_2$ for at least 24 hours before use.

About 800 HESC colony pieces are plated to a 100 mm dish with a MEF feeder layer, as described above. The dish contains an appropriate amount of CKSR medium and is incubated at 37° C. for 4-6 days at 5% $CO_2$. After 4-6 days, the hESC colonies are between about 1 and 2 mm in diameter. At this time, the HESC colonies are passaged, typically one plate is split into three.

Conditioned or unconditioned KSR HESC media is warmed in a water bath to 37° C. Freshly thawed 1M β-mercaptoethanol is added to a final concentration of 0.1 mM. The dish is placed on a dissecting microscope. A stem cell culture tool, such as the tool 100 of FIG. 1, is rolled over each cell colony to cut the colony into a grid. Typically, each cell colony is cut twice, once in each of perpendicular directions. Using a fire drawn Pasteur pipette needle or a P1000 pipette tip, colony pieces are transferred to a fresh MEF feeder dish containing an appropriate amount of CKSR or 20% KSR HESC medium. The cells are fed with fresh medium the day after plating and every second day after that. The incubation and passaging process is repeated as desired to produce a desired amount of hESCs.

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

I claim:

1. A method of dissecting a substrate of cultured cells, comprising:
    separating the substrate of cultured cells into separated portions with a cutting tool that comprises a rotatable shaft having a shallow thread member that forms a continuous groove extending around the rotatable shaft and across a width of the rotatable shaft, the continuous groove extending upward on both sides into sharp crests that define a continuous cutting surface across the width of the rotatable shaft, the continuous groove comprising a shallow, concavely curved surface that has a generally constant thread height across a width of the rotatable shaft, wherein the sharp crests of the continuous cutting surface are rolled through the substrate to cut the substrate into the portions without collecting a substantial amount of substrate in the shallow, concavely curved surface of the continuous groove; and
    separating the portions from one another to dissect the substrate.

2. The method of claim 1, wherein the continuous cutting surface is rolled through the substrate in at least two different intersecting pathways to subdivide the portions of the substrate into sub-portions.

3. The method of claim 2, wherein the two different intersecting pathways are at least substantially perpendicular to one another, such that the sub-portions into which the substrate is cut are at least substantially rectangular sub-portions.

4. The method of claim 2, further comprising transferring the sub-portions to a container comprising culture medium.

5. The method of claim 1, wherein the shaft is a first shaft and the first shaft is coupled to a handle, further comprising:
    removing the first shaft from the handle;
    attaching a second shaft to the handle, the second shaft having a second continuous cutting surface extending around the second shaft; and
    separating a second substrate of cultured cells into separated portions by rolling the second continuous cutting surface through the second substrate to cut the second substrate into portions.

6. The method of claim 5, wherein the first shaft comprises a first type of continuous cutting surface and the second shaft comprises a second type of continuous cutting surface, the first type of continuous cutting surface being different than the second type of continuous cutting surface.

7. The method of claim 1, wherein the cutting tool further comprises a handle, and the continuous cutting surface is rolled through the substrate by grasping the handle, frictionally engaging the continuous cutting surface with the substrate, and advancing the cutting tool through the substrate.

8. The method of claim 1, wherein the substrate comprises stem cell colonies, further comprising culturing at least one stem cell colony to a cross section of at least about 1 mm.

9. The method of claim 1, wherein the substrate comprises cultured embryonic stem cells, and the method comprises at least partially segregating embryonic stem cells in the substrate into sub-groups.

10. The method of claim 1, wherein the substrate comprises embryoid bodies, and the method comprises dissecting the embryoid bodies with the cutting blade.

11. The method of claim 1, wherein the substrate is a first substrate and comprises culture medium, the method further comprising:
    transferring stem cells to the first substrate;
    incubating the first substrate until the stem cells form stem cell colonies having a cross section of at least about 1 mm;
    transferring the stem cell colony pieces to a second substrate comprising culture medium; and
    incubating the second substrate.

12. The method of claim 1, wherein the continuous cutting surface is helically disposed about the shaft.

13. The method of claim 1, wherein the shaft has an axial length of at least about 5 mm and a radial width of between about 2 mm and about and the thread member comprises:
    (A) a thread pitch of between about 150 μm and 1000 μm;
    (B) a lead angle of less than about 45 degrees; and
    (C) a thread height of at least about 0.2 mm.

14. The method of claim 1, wherein a crest width of the sharp crests is less than about 2 μm.

* * * * *